United States Patent
Tchir et al.

(10) Patent No.: US 9,202,014 B2
(45) Date of Patent: Dec. 1, 2015

(54) REDUCTION OF FOULING IN HIGH PRESSURE REACTORS

(71) Applicant: NOVA Chemicals (International) S.A., Fribourg (CH)

(72) Inventors: William Joseph Tchir, Calgary (CA); Eric Cheluget, Prospect Heights, IL (US)

(73) Assignee: NOVA Chemicals (International) S.A., Fribourg (CH)

( * ) Notice: Subject to any disclaimer, the term of this patent is extended or adjusted under 35 U.S.C. 154(b) by 223 days.

(21) Appl. No.: 14/078,576

(22) Filed: Nov. 13, 2013

(65) Prior Publication Data

US 2014/0155568 A1    Jun. 5, 2014

(30) Foreign Application Priority Data

Dec. 5, 2012 (CA) ................. 2798036

(51) Int. Cl.
*G06F 7/60* (2006.01)
*C08F 2/00* (2006.01)
*C08F 210/00* (2006.01)
*G06F 19/00* (2011.01)
*C08F 110/02* (2006.01)

(52) U.S. Cl.
CPC ............ *G06F 19/702* (2013.01); *C08F 110/02* (2013.01)

(58) Field of Classification Search
CPC ...... G06F 19/702; C08F 110/02; C08F 10/02; C08F 2/00; C08F 2/14
USPC ........................ 526/64, 348; 703/2
See application file for complete search history.

(56) References Cited

U.S. PATENT DOCUMENTS

| | | | |
|---|---|---|---|
| 2,153,553 | A | 4/1939 | Fawcett et al. |
| 3,334,081 | A | 8/1967 | Madgwick et al. |
| 3,399,185 | A | 8/1968 | Schappert |
| 3,917,577 | A | 11/1975 | Trieschmann et al. |
| 4,135,044 | A | 1/1979 | Beals |
| 6,727,326 | B2 | 4/2004 | Mahling et al. |
| 7,354,979 | B2 | 4/2008 | Brant et al. |
| 7,650,930 | B2 | 1/2010 | Cheluget et al. |
| 2009/0062495 | A1* | 3/2009 | Cheluget et al. ............. 526/335 |

OTHER PUBLICATIONS

Ehrlich, P. and Mortimer, G. A.; Fundamentals of the Free-Radical Polymerization of Ethylene; Adv. Polymer Sci., vol. 7, pp. 386-448 (1970).

Lacombe, Robert H. and Sanchez, Isaac C.; Statistical Thermodynamics of Fluid Mixtures; The Journal of Physical Chemistry, vol. 80, No. 23, 1976, pp. 2568-2580.

Sanchez, Isaac C. and Lacombe, Robert H.; Statistical Thermodynamics of Polymer Solutions; Macromolecules, vol. 11, No. 6, Nov.-Dec. 1978, pp. 1145-1156.

(Continued)

*Primary Examiner* — William Cheung
(74) *Attorney, Agent, or Firm* — Julie L. Heinrich

(57) ABSTRACT

The Application of equations of state to experimental and literature data permits the formation of a model and phase diagram(s) that show under what conditions polyethylene is likely to precipitate out of a high pressure solution of polyethylene in supercritical ethylene. This then permits a better definition to run a high pressure reactor to reduce the likelihood of phase separation, loss of cooling and potentially decomposition of the reactor contents.

11 Claims, 8 Drawing Sheets

(56) References Cited

OTHER PUBLICATIONS

Gross, Joachim and Sadowski, Gabriele; Perturbed—Chain SAFT: An Equation of State Based on a Perturbation Theory for Chain Molecules; Ind. Eng. Chem. Res. 2001, 40, pp. 1244-1260; Published on Web Jan. 18, 2001.

Orbey, Hasan; Bokis, Costas P. and Chen, Chau-Chyun; Equation of State Modeling of Phase Equilibrium in the Low-Denisty Polyethylene Process: The Sanchez-Lacombe, Statistical Associating Fluid Theory and Polymer-Soave-Redlich-Kwong Equations of State; Ind. Eng. Chem. Res. 1998, 37, pp. 4481-4491; published on Web Sep. 30, 1998.

Chan, Alan Ka Chun; Adidharma, Hertanto and Radosz, Maciej; Fluid-Liquid Transitions of Poly(ethylene-co-octene-1) in Supercritical Ethylene Solutions; Ind. Eng. Chem. Res. 2000, 39, pp. 4370-4375; Published on Web Oct. 4, 2000.

Trumpi, H.; De Loos, Th. W.; Krenz, R.A. and Heidemann, R.A.; High pressure phase equilibria in the system linear low density polyethylene + ethylene: experimental results and modelling; J. of Supercritical Fluids 27 (2003); pp. 205-214.

Chapman, Walter G.; Gubbins, Keith E.; Jackson, George and Radosz, Maciej; New Reference Equation of State for Associating Liquids; Ind. Eng. Chem. Res. 1990, 29, pp. 1709-1721.

Huang, Stanley H. and Radosz, Maciej; Equation of State for Small, Large, Polydisperse, and Associating Molecules; Ind. Eng. Chem. Res. 1990, 29, pp. 2284-2294.

Huang, Stanley H. and Radosz, Maciej; Equation of State for Small, Large, Polydisperse, and Associating Molecules; Extension to Fluid Mixtures; Ind. Eng. Chem. Res., 1991, 30, pp. 1994-2005.

Muller, Erich W. and Gubbins, Keith E.; Molecular-Based Equations of State for Associating Fluids: A Review of SAFT and Related Approaches; Ind. Eng. Chem. Res. 2001, 40, pp. 2193-2211.

Chen, Stephen S. and Kreglewski, Aleksander; Applications of the Augmented van der Waals Theory of Fluids. I. Pure Fluids; Bd. 81, Nr. 10, 1977, pp. 1048-1052.

Boublik, Tomas; Hard-Sphere Equation of State; AIP/The Journal of Chemicals Physics 53, (1970); pp. 471-472.

Monsoori, G.A./ Carnahan, N.F.; Starling, K.E. and Leland, T.W., Jr.; Equilibrium Thermodynamic Properties of the Mixture of Hard Spheres; AIP/The Journal of Chemical Physics 54; (1971), pp. 1523-1525.

Boublik, Thomas; 5. Perturbation Theory; Equations of State for Fluids and Fluid Mixtures; 2000 International Union of Pure and Applied Chemistry; pp. 127-168.

Barker, J.A. and Henderson, D.; Perturbation Theory and Equation of State for Fluids. II. A Successful Theory of Liquids; The Journal of Chemical Physics, vol. 47, No. 11, Dec. 1, 1967; pp. 4714-4721.

\* cited by examiner

REDUCTION OF FOULING IN HIGH PRESSURE REACTORS

FIELD OF THE INVENTION

The present invention relates to the field of high pressure polymerization of alpha olefins, and, for example, ethylene and co- and homo-polymers thereof. For example, the present invention relates to the process for the polymerization in tubular reactors at high temperatures and pressures.

BACKGROUND OF THE INVENTION

U.S. Pat. No. 2,153,553 issued Apr. 11, 1939 discloses the high pressure polymerization of ethylene. The patent sets forth four conditions that must be met for the polymerization of ethylene to solid polymers. The pressure should be above 500 atmospheres, the temperature should be between 100 and 400° C. The oxygen content of the reactants must not exceed a very small critical amount, and there must be sufficient thermal control of the reaction to avoid undue rise in temperature. The patent then contains a caution. If the four conditions are not properly met there is either no reaction or there is an undesired reaction of explosive violence giving rise to carbon and methane. The latter is sometimes euphemistically referred to as a "decomp".

During polymerization it has been observed that there may be a period where heat transfer from the reaction to the cooling jacket is impaired. Given the warning above it is imperative to either not impair the cooling capacity or to quickly restore the cooling capacity of the cooling jacket if it is impaired. It is believed that this loss of cooling efficiency is caused by deposition of polymer on the internal reactor wall. The current methods of removing polymer deposits from the internal reactor wall are primarily physical (i.e. send a pressure shockwave along the tube to dislodge any polymer residue).

Additionally, some operators may cycle the jacket temperatures from normal set points to about 150-200° C. for a several hours, in an attempt to dissolve or shed polymer deposits on the internal walls of the reactor.

In the operation of a high pressure polyethylene plant there are a number of conflicting desiderata. To achieve highest conversion one may set a high difference in temperature between the reactants and the cooling medium in the reactor shell (jacket) temperature. On the other hand, one may want to know at what temperatures polymer is likely to precipitate on the internal wall of the reactor leading to a number of potential consequences including reactor wall fouling, loss of cooling, formation of gels and ultimately a decomposition of the contents of the reactor.

SUMMARY OF THE INVENTION

In one embodiment, the invention provides a method to determine the liquid liquid equilibrium boundary and the critical polymer concentration as a function of molecular weight distribution (MWD) for a multitude of different products comprising from about 80 to about 100 wt. % of ethylene and about 0 up to about 20 weight % of one or more $C_{3-8}$ alpha olefins having a weight average molecular weight from about 8,000 to about 500,000 (which includes a minor component having a molecular weight of about 500,000 or greater) produced in super critical ethylene in a high pressure reactor at temperatures from about 80° C. to about 350° C. and pressures from about 100 MPa to about 350 MPa comprising:

1—modeling experimental or literature data for the liquid liquid equilibrium using an equation of state model (for example, the Sanchez-Lacombe or the perturbed chain statistical associating fluid theory equation of state to describe the effects of the molecular weight and the polydispersity of the polyethylene on the liquid liquid equilibrium curve 2—determining the composition-specific parameters of the model from 1; and 3—applying the resultant equation of state model to the temperature, pressure and composition conditions of the reaction to generate the liquid liquid equilibrium boundary and optionally the critical polymer concentration (as used herein "the critical polymer concentration" means the point below which droplets of a phase with a higher concentration in polymer are formed and above which droplets primarily of solvent (i.e. ethylene) are formed).

In a further embodiment the reactor is a tubular reactor.

In a further embodiment there is provided a method to prepare a liquid polymer lean/liquid polymer rich and liquid liquid phase diagram for a reactor for polymerizing a system comprising a polymer having a weight average molecular weight from about 8,000 to about 500,000 comprising from about 80 to about 100 wt % of ethylene and about 0 to about 20 wt % of one or more $C_{3-8}$ alpha olefins in super critical liquid ethylene at temperatures from about 80° C. to about 350° C. and pressures from about 100 MPa to about 350 MPa to define operating conditions at which the polymer is substantially dissolved in the liquid phase comprising:

a) preparing a phase diagram for liquid polymer lean/liquid polymer rich for said reactor and process at temperatures from about 150° C. to about 350° C. and pressures from about 100 to about 350 MPa;

b) inserting into said phase diagram a liquid liquid phase boundary determined as above.

As used herein the polymer is substantially dissolved in the liquid phase if great than about 90% of the polymer is dissolved in the liquid phase. In another embodiment, greater than about 95% of the polymer may be dissolved in the liquid phase. In another embodiment, greater than about 98% of the polymer may be dissolved in the liquid phase. In another embodiment, greater than about 99% of the polymer may be dissolved in the liquid phase. In another embodiment, 100% of the polymer may be dissolved in the liquid phase.

In a further embodiment there is provided a method for conducting the polymerization of a polymer having a weight average molecular weight from about 8,000 to about 500,000 comprising about 80 to about 100 wt % of ethylene and about 0 to about 20 wt % of one or more $C_{3-8}$ alpha olefins in super critical liquid ethylene at temperatures from about 80° C. to about 350° C. and pressures from about 100 MPa to about 350 MPa to define operating conditions at which the polymer is substantially dissolved in the liquid phase comprising monitoring the heat balance of said reaction and determining when there is an apparent loss of cooling and comparing the operating conditions to the above phase diagram and adjusting one or more of the temperature and pressure conditions to bring the operating conditions more than about 5% within the liquid area of the phase diagram.

In a further embodiment the operating conditions are adjusted to bring them within the liquid area of the phase diagram by more than about 10%.

In a further embodiment the phase diagram is digitized and stored on a microprocessor and heat balance for the reaction is monitored using a microprocessor and the operating conditions are adjusted using a microprocessor.

In a further embodiment there is provided a method to extend the run time between cleanings of a high pressures reactor for the polymerization of the polymerization of a polymer having a weight average molecular weight from about 8,000 to about 500,000 comprising about 80 to about 100 wt % of ethylene and about 0 to about 20 wt % of one or more $C_{3-8}$ alpha olefins in super critical ethylene at temperatures from about 80° C. to about 350° C. and pressures from about 100 MPa to about 350 MPa comprising operating as described above, so that not more than about 30 minutes elapse between the apparent loss of cooling and achieving the new operating conditions within the liquid area within the phase diagram.

In a further embodiment the time to achieve the adjusted operating conditions is less than about 15 minutes.

In a further embodiment there is provided a method to dissolve precipitated polymer in a high pressures reactor for the polymerization of the polymerization of a polymer having a weight average molecular weight from about 8,000 to about 500,000 comprising about 80 to about 100 wt % of ethylene and about 0 to about 20 wt % of one or more $C_{3-8}$ alpha olefins in super critical liquid ethylene at temperatures from about 80° C. to about 350° C. and pressures from about 100 MPa to about 350 MPa comprising operating as outlined above, so that not more than about 30 minutes elapse between the apparent loss of cooling and achieving the new operating conditions within the liquid area within the phase diagram.

In a further embodiment the phase diagram is digitized and stored on a microprocessor and heat balance for the reaction is monitored using a microprocessor and the operating conditions are adjusted using a microprocessor.

In a further embodiment the time to achieve the adjusted operating conditions is less than about 15 minutes.

BRIEF DESCRIPTION OF THE DRAWINGS

In FIG. 1 the area above a plot is a single phase region while the area below a plot is a two phase region.

DETAILED DESCRIPTION

Figure 1:
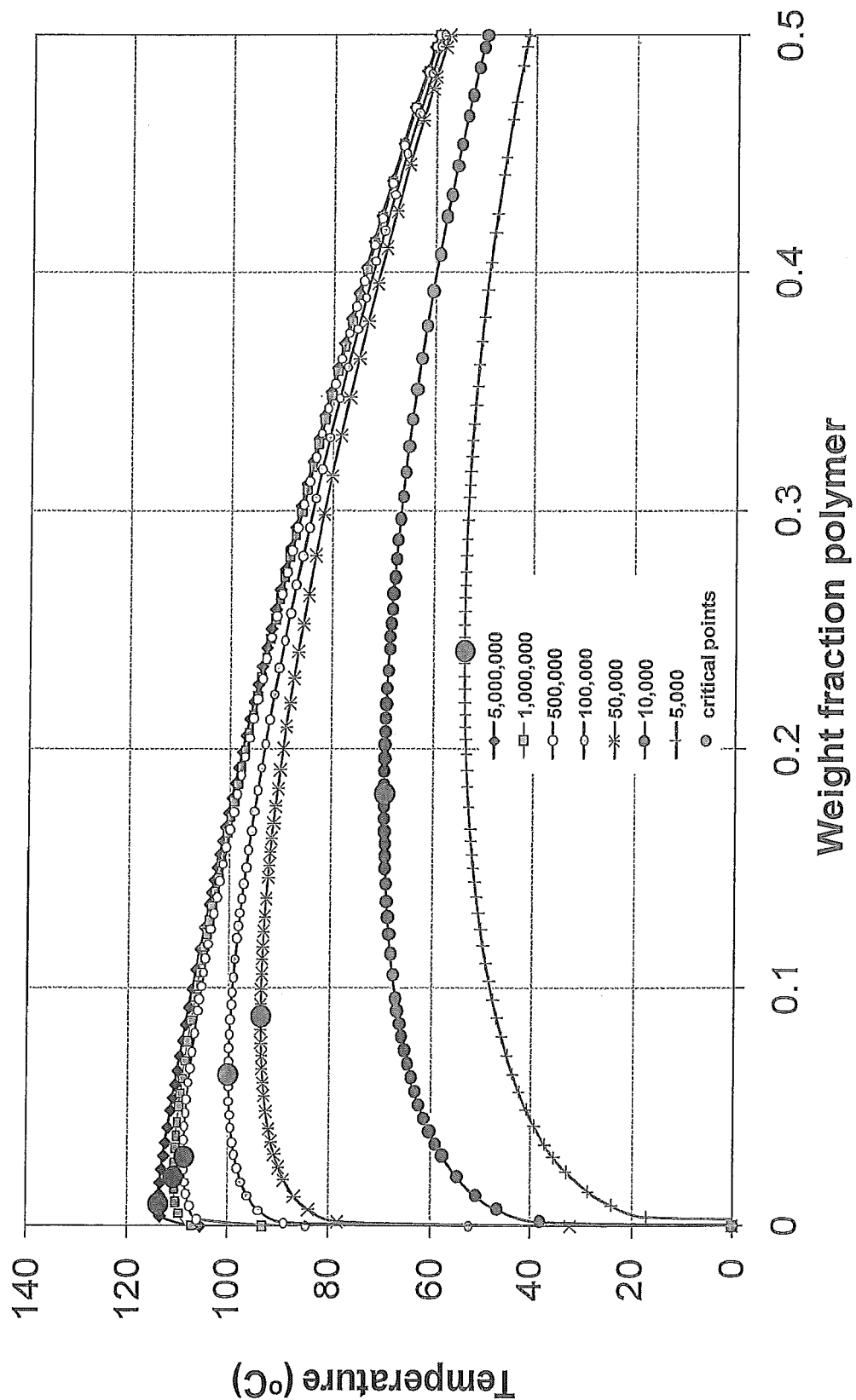
FIG. 1 is a calculated plot of the effect of molecular weight on the isobaric phase diagram for the ethylene-polyethylene system at 210 MPa, based on the Sanchez-Lacombe equation of state with monodisperse polymer.

Other than in the operating examples or where otherwise indicated, all numbers or expressions referring to quantities of ingredients, reaction conditions, etc. used in the specification and claims are to be understood as modified in all instances by the term "about." Accordingly, unless indicated to the contrary, the numerical parameters set forth in the following specification and attached claims are approximations that can vary depending upon the desired properties, which the present invention desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

All compositional ranges expressed herein are limited in total to and do not exceed 100 percent (volume percent or weight percent) in practice. Where multiple components can be present in a composition, the sum of the maximum amounts of each component can exceed 100 percent, with the understanding that, and as those skilled in the art readily understand, that the amounts of the components actually used will conform to the maximum of 100 percent.

In one embodiment, the present invention is directed to temperature and pressures regimes at which droplets of high molecular weight polymer (that is weight average molecular weight of about 500,000 or greater) may separate from the polymer solution. The polymer may precipitate on to the inner surface of the reactor walls. This may result in a number of issues. For example, the run time between reactor cleanings may be shortened. Product quality may be impaired due to contamination by deposited polymer coming off the reactor wall. There may also be a "decomp".

In one embodiment, the present invention seeks to provide a method to generate a liquid liquid equilibrium curve for high pressure polyethylene and its homologues.

Once the liquid liquid equilibrium curve is generated it will be understood that phase separation and conversion are integrally related. One may operate the reactor at a wall temperature of 130° C.±5° C. in a portion of the first reaction zone, that is, at low conversions (low polymer concentrations) to prevent liquid liquid phase separation. The need to keep the reactor contents hot is governed by the critical polymer concentration; beyond that critical point, droplets composed of substantially only ethylene, i.e. with minimal amounts of polymer, form in a continuous polymer solution phase. These solvent droplets will not lead to fouling of the inner surface of the internal reactor wall, and may act to improve heat transfer.

In one embodiment, the present invention relates to the production of high pressure, low density polyethylene (LDPE). The polyethylene comprises from about 100 to about 80 weight %, or from about 100 to about 90 wt. %, or from about 100 to about 95 wt. % of ethylene and from about 0 to about 20 wt. %, or about 0 to about 10 wt. %, or from about 0 to about 5 wt. % of one or more monomers selected from $C_{3-8}$. In another embodiment the one or more monomers are selected from $C_{3-4}$ alpha olefins. In one embodiment the alpha olefins include propylene, butene, hexene and octene. In another embodiment, the olefins include propylene and butene.

Although the process has been modified over time it essentially comprises compressing ethylene to a high enough pressure so that it becomes a supercritical fluid. The pressures range from about 100 to about 350 MPa (e.g., about 14,500 to about 50,800 psi) or from about 200 to about 300 MPa (about 29,000 psi to about 43,500 psi) and the temperature ranges from about 80° C. to about 350° C., or from about 150° C. to about 325° C. The supercritical ethylene together with one or more of initiators, chain transfer agent and optional comonomers are fed to a high pressure reactor. The reactor may be an autoclave reactor or for example, a tubular reactor. Tubular reactors may have a length from about 200 m to about 2500 m, and a diameter from about 20 mm to about 100 mm.

Thermocouples along the length of the reactor may be spaced at a distance from about 5 to about 15, or about 8 to about 12, or from about 8 to about 11 meters. In some embodiments there may be from about 100 and about 350 thermocouples, or from about 120 to about 300 thermocouples spaced along the length of the reactor. The spacing of the thermocouples may be uniform along the length of the reactor. In some embodiments the spacing of the thermocouples may not be uniform along the length of the reactor.

Generally there are a number of injection points spaced along the tubular reactor where additional components such as initiators, chain transfer agents, and monomers (for example cold monomers), may be added to the reactor. The design and operation of tubular reactors is illustrated by a number of patents including for example U.S. Pat. No. 3,334, 081 issued Aug. 1, 1967 to Madgwick et al, assigned to Union Carbide Corporation; U.S. Pat. No. 3,399,185 Issued Aug. 27, 1968 to Schappert assigned to Koppers Company, Inc., U.S. Pat. No. 3,917,577 issued Nov. 4, 1975 to Trieschmann et al. assigned to Badische Anilin & Soda-Fabrik Aktiengesellschaft; and U.S. Pat. No. 4,135,044 issued Jan. 16, 1979 to Beals assigned to Exxon Research & Engineering Co.

There may be a number of injection points for a high pressure polyethylene reactor. However, as will be discussed below the issue is not injection points. Rather the issue is conversion. As shown in FIG. 1 the phase separation temperature for monodisperse polyethylene from reactants (liquid ethylene) at pressures of about 210 MPa increases with polymer concentration to about 115° C., at a polymer concentration of about 1 wt %, for a polymer having a molecular weight greater than about 1,000.000. Thereafter the phase separation temperature falls. The above temperature is derived from a theoretical calculation and to provide operating safety margins tone may operate the reactor at pressures from about 100 MPa to about 350 MPa, or from about 150 MPa to about 325 MPa, or from about 200 MPa to about 300 MPa, so that during the initial conversion of ethylene to polyethylene of up to about 10 weight %, or up to about 8 weight %, or up to about 7 weight % of polyethylene the reaction temperature is maintained above about 125 to about 135° C., or above about 130° C., or above about 128° C.

Generally the initiator, or mixture of initiators, is injected into the reactor in amounts from about 100 to about 500 ppm, or from about 125 to about 425, (based on the weight of the reactants). The initiator(s) may be selected from oxygen, peroxides, persulphates, perborates, percarbonates, nitriles, and sulphides (methyl vinyl sulphide). Some free radical initiators can be selected from the list given in Ehrlich, P., et al., Fundamentals of the Free-Radical Polymerization of Ethylene, Advances in Polymer Science, Vol. 7, pp. 386-448, (1970).

Non-limiting examples of some free radical producing substances include oxygen (air); peroxide compounds such as hydrogen peroxide, decanoyl peroxide, t-butyl peroxy neodecanoate, t-butyl peroxypivalate, 3,5,5-trimethyl hexanoyl peroxide, diethyl peroxide, t-butyl peroxy-2-ethyl hexanoate, t-butyl peroxy isobutyrate, benzoyl peroxide, t-butyl peroxy acetate, t-butyl peroxy benzoate, di-t-butyl peroxide, and 1,1, 3,3-tetramethyl butyl hydroperoxide; alkali metal persulfates, perborates and percarbonates; and azo compounds such as azo bis isobutyronitrite. n one embodiment, initiators are selected from oxygen (air) and organic peroxides.

A chain transfer agent (sometimes referred to as a telogen or a modifier) may also be present in the reactants. The chain transfer agent may be added at one or more points along the tubular reactor. Some chain transfer agents include the saturated aliphatic aldehydes, such as formaldehyde, acetaldehyde and the like, the saturated aliphatic ketones, such as acetone, diethyl ketone, diamyl ketone, and the like, the saturated aliphatic alcohols, such as methanol, ethanol, propanol, and the like, paraffins or cycloparaffins such as pentane, hexane, cyclohexane, and the like, aromatic compounds such as toluene, diethylbenzene, xylene, and the like, and other compounds which act as chain terminating agents such as carbon tetrachloride, chloroform, etc.

The chain transfer agent may be used in amounts from about 0.20 to about 2, or from about 0.24 to about 1 mole percent based on the total ethylene feed to the reactor.

Phase diagrams for the liquid-liquid phase separation of monodisperse polyethylene and supercritical ethylene are known, at the temperature and pressures ranges for a low density polyethylene reactor, however as far as Applicant is aware there has been no recognition of the effects on reactor operation of liquid-liquid phase separation to form droplets of high molecular weight polymer below the critical polymer concentration. The problem is to determine the liquid-liquid equilibrium boundary and optionally the critical polymer concentration as a function of the molecular weight distribution of the polymer.

Suitable equation of state models include lattice-fluid models such as Flory-Huggins and the Sanchez-Lacombe equation of state (Lacombe R. H.; Sanchez, I. C. Statistical Thermodynamics of Fluid Mixtures. J. Phys. Chem. 1976, 80 (23), 2568-2580; Sanchez, I. C.; Lacombe, R. H. Statistical thermodynamics of polymer solutions. Macromolecules 1978, 11 (6), 1145-1156), as well as models based on thermodynamic perturbation theory, for example, the perturbed chain statistical associating fluid theory equation of state (Gross, J.; Sadowski, G, Perturbed-Chain SAFT: An Equation of State Based on a Perturbation Theory for Chain Molecules, Ind. Eng. Chem. Res., 2001, 40, 1244). Variants of that model (e.g. SAFT-VR, SAFT-LJ, soft-SAFT, SW-PC-SAFT, CK-PC-SAFT, or GC-SAFT-VR), or TPT1 and variations on this more general approach, such as TPT1-MSA and TPT1-RHNC may also be appropriate, as would thermodynamic perturbation theories involving higher-than-first-order terms. Augmented cubic equations of state such as the Polymer-Soave-Redlich-Kwong equation of state (Hasan Orbey; Costas P. Bokis; Chau-Chyun Chen, Equation of State Modeling of Phase Equilibrium in the Low-Density Polyethylene Process: The Sanchez-Lacombe, Statistical Associating Fluid Theory, and Polymer-Soave-Redlich-Kwong Equations of State, Ind. Eng. Chem. Res., 1998, 37 (11), pp 4481-4491) may have similar utility.

The Sanchez-Lacombe equation of state has been well known for at least 20 years to those skilled in the art. This equation has the form $$\frac{P}{RT} = \frac{(1-d)}{(v+c)} - \frac{d^2}{b} \ln\left(\frac{v+c-b/d}{v+c}\right) - \frac{a}{RT(v+c)^2} \quad (1)$$

where T is the temperature, P is the pressure, R is the ideal gas constant, v is the molar volume, and a, b, c, d are mixture parameters. The mixture parameters are given by the following mixing rules $$a = \sum_{i=1}^{n_c}\sum_{j=1}^{n_c} x_i x_j d_i d_j v_{ij} \varepsilon_{ij}(1-k_{ij}) \quad (2)$$

where $x_i$ is the mole fraction of component i and there are $n_c$ components. The binary interaction parameter, $k_{ij}$, is dependent on temperature, $k_{ij}=k_{ij}^a+k_{ij}^b T$ and $d_i$ is a pure compound parameter related to the number of lattice sites occupied by a molecule. It is a linear function of molecular weight and is often expressed as $$\frac{d_i}{M_i}$$

where $M_i$ is the molecular weight. The cross parameters are given by $$v_{ij} = \frac{(v_{ii}+v_{jj})}{2} \quad (3)$$

where $v_{ii}$ is a pure compound parameter related to the size of a lattice site, and $$\varepsilon_{ij}=\sqrt{\varepsilon_{ii}\varepsilon_{jj}} \quad (4)$$

where $\varepsilon_{ii}$ is a pure compound lattice energy parameter. The b parameter is calculated as $$b = \sum_{i=1}^{n_c}\sum_{j=1}^{n_c} x_i x_j d_i d_j v_{ij} \quad (5)$$

while the d parameter is $$d = \sum_{i=1}^{n_c} x_i d_i \quad (6)$$

The volume shift parameter is introduced to give better density predictions $$c = \sum_{i=1}^{n_c} x_i c_i \quad (7)$$

Polymer components are polydisperse, with a molecular weight distribution (MWD) curve characterized using Size Exclusion Chromatography (SEC). The MWD distribution curve can be converted to a set of i pseudocomponents with weight fractions $w_i$ using the relationship:

$$w_i = \int_{\log M_{i-1}}^{\log M_i} \frac{dWF}{d\log M} d\log M \quad (8)$$

The number-average molecular weight of the pseudocomponent $\overline{M}_{Ni}$ is determined using the expression:

$$\overline{M}_{Ni} = \frac{w_i}{\int_{\log M_{i-1}}^{\log M_i} \frac{1}{10^{\log M_i}} \frac{dWF}{d\log M} dM} \quad (9)$$

For polydisperse polymers, the SEC data were converted to a set of 100 pseudocomponents using equations (8) and (9). The integrations in these equations were performed using the TableCurve 2D™ software. The pseudocomponents are then used in phase equilibrium calculations using VLXE software (VLXE ApS, Copenhagen, Denmark).

For application of this equation of state to this system, the parameters were regressed based on a compromise between two sets of experimental data. The first data set was obtained from Chan and co-workers (Chan, A. K. C.; Adidharma, H.; Radosz, M., Fluid-liquid Transitions of Poly(ethylene-co-octene-1) in Supercritical ethylene Solutions, *Ind. Eng. Chem. Res.* 2000, 39, 4370. These data are significant because the polymer is close to being monodisperse with a molecular weight of 32,000. A second data set was Trumpi, H.; de Loos, Th. W.; Krenz, R. A.; Heidemann, R. A., High Pressure Phase Equilibria in the System Linear Low Density Polyethylene+Ethylene: Experimental results and Modeling., *J. Supercritical Fluids,* 2003, 27(2), 205. These data are for a polymer having a molecular weight distribution which may be represented by 7 pseudocomponents.

The results of the parameter regression are described in Table 1.

TABLE 1

Values of parameters used in the Sanchez-Lacombe equation of state

| Parameter | Polyethylene | Ethylene |
|---|---|---|
| Lattice energy parameter, $\varepsilon_{ii}$, K | 495.2 | 275.24 |
| Volume occupied per lattice site, $v_{ii}$ cm$^3$/mol | 8.9838 | 7.4714 |
| Number of lattice sites occupied, $\frac{d_i}{M_i}$ | 0.06989 | 0.22713 |
| Volume shift parameter, $\frac{c_i}{M_i}$, mol/g | −0.4658 | |
| Binary interaction parameter | $k_{ij}$ (T) = 0.00904−0.0002892T(K) | |

The Sanchez-Lacombe equation of state, with the parameters in Table 1, was applied to the polyethylene/supercritical ethylene system. FIG. 1 illustrates the predicted effect of molecular weight of a monodisperse polymer on the location of the cloud point curve at 210 MPa. The molecular weight was varied from a low value of 5000 to a high value of 5,000,000. The figure indicates that increasing the molecular weight increases the size of the two-phase region of the phase diagram. A temperature of at least about 115° C. may be used to keep an about 5,000,000 molecular weight polymer in single phase at all compositions; this drops to about 100° C. for a molecular weight of about 100,000 and to about 70° C. for a molecular weight of about 10,000.

The Sanchez-Lacombe equation of state was also applied to polydisperse polymers in supercritical ethylene. Phase boundary calculations were performed for four different commercial grades of low density polyethylene, with melt index in the range of about 0.25 to about 25. The particular focus was on the about 0.25 melt index grade, since this product was known to have a higher propensity for reactor fouling.

Figure 2:
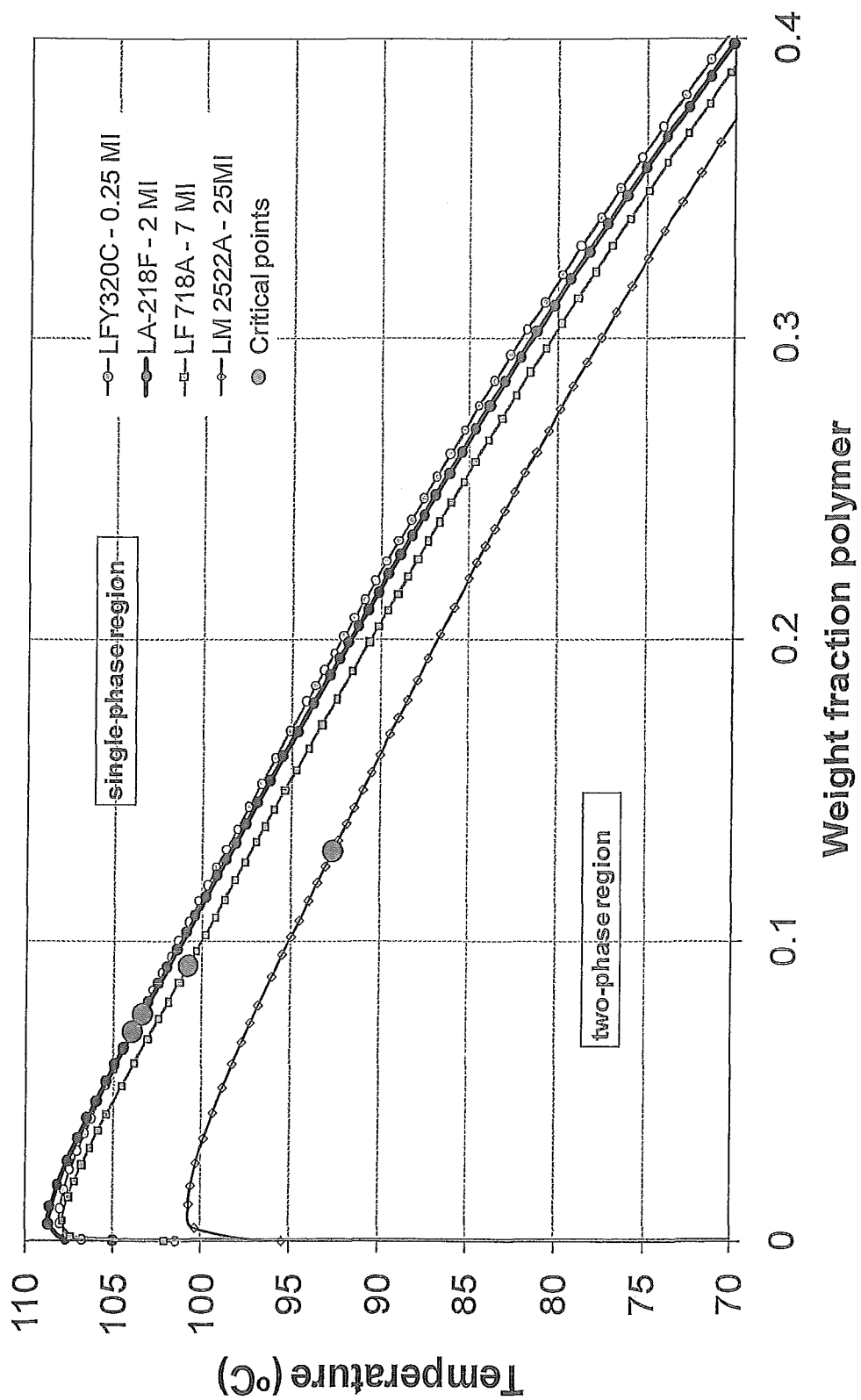
FIG. 2 is a calculated plot of the isobaric liquid-liquid phase boundaries (cloud point curves) for four commercial polyethylenes at 210 MPa, based on the Sanchez-Lacombe equation of state.

FIG. 2 is a calculated plot of the isobaric liquid-liquid phase boundaries for the four commercial polyethylenes. LFY320C resin has the highest cloud point temperature, as expected, because it has the highest proportion of high molecular weight material. A temperature of about 110° C. is sufficient to keep this polymer from phase separating, and the critical polymer concentration for this product is approximately 7 wt %. The cloud point curves for the other resins are lower in temperature compared to LFY320C, and decrease monotonically with melt index.

Figure 3:
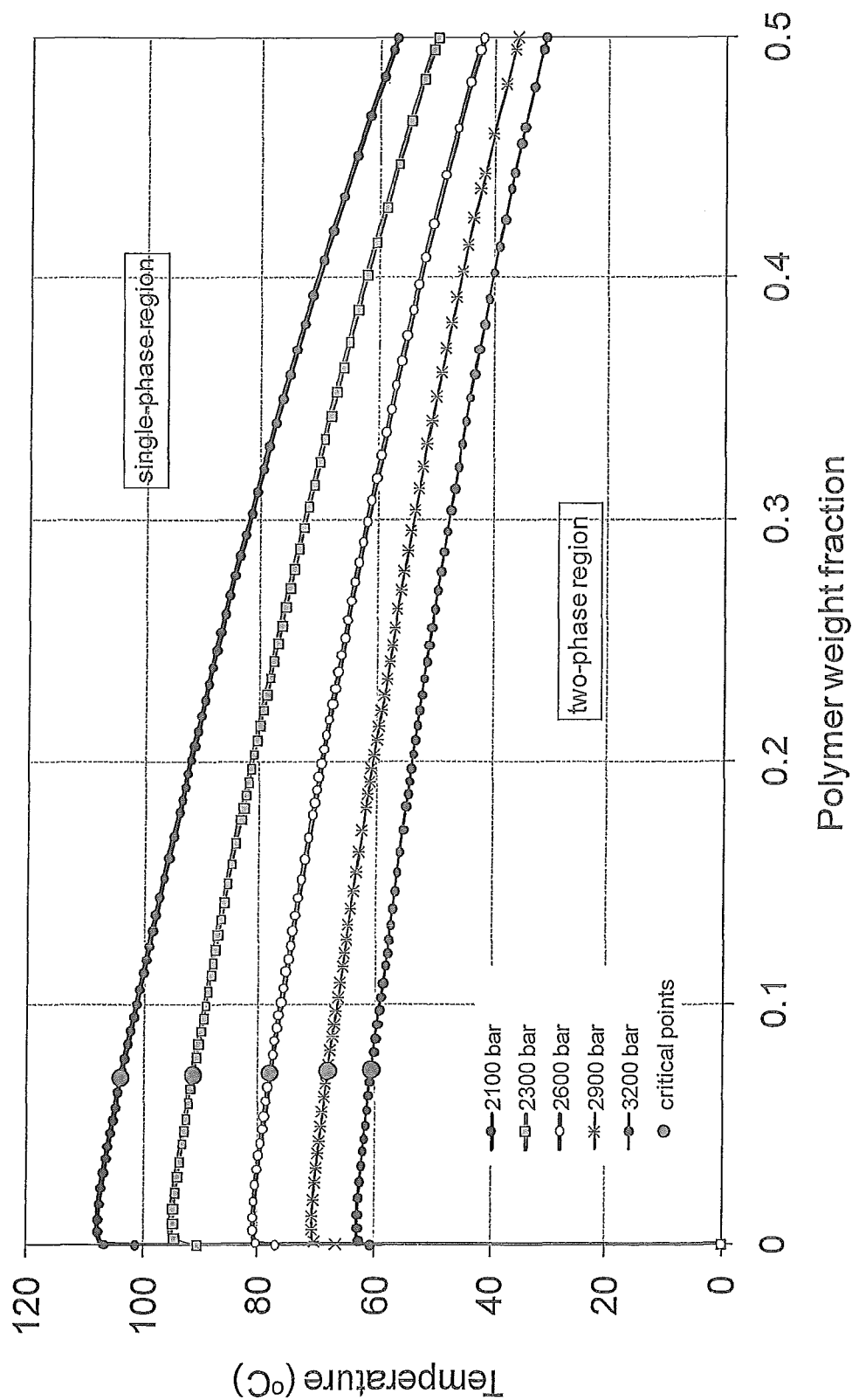
FIG. 3 is a calculated plot of the isobaric liquid-liquid phase boundary for commercial polyethylene LFY320C as a function of pressure, based on the Sanchez-Lacombe equation of state.

FIG. 3 is a calculated plot of the isobaric liquid-liquid phase boundaries for the LFY320C resin as a function of pressure. The phase boundary shifts to lower temperatures as the pressure is increased, indicating that the solvent quality of supercritical ethylene improves with pressure.

Figure 4:
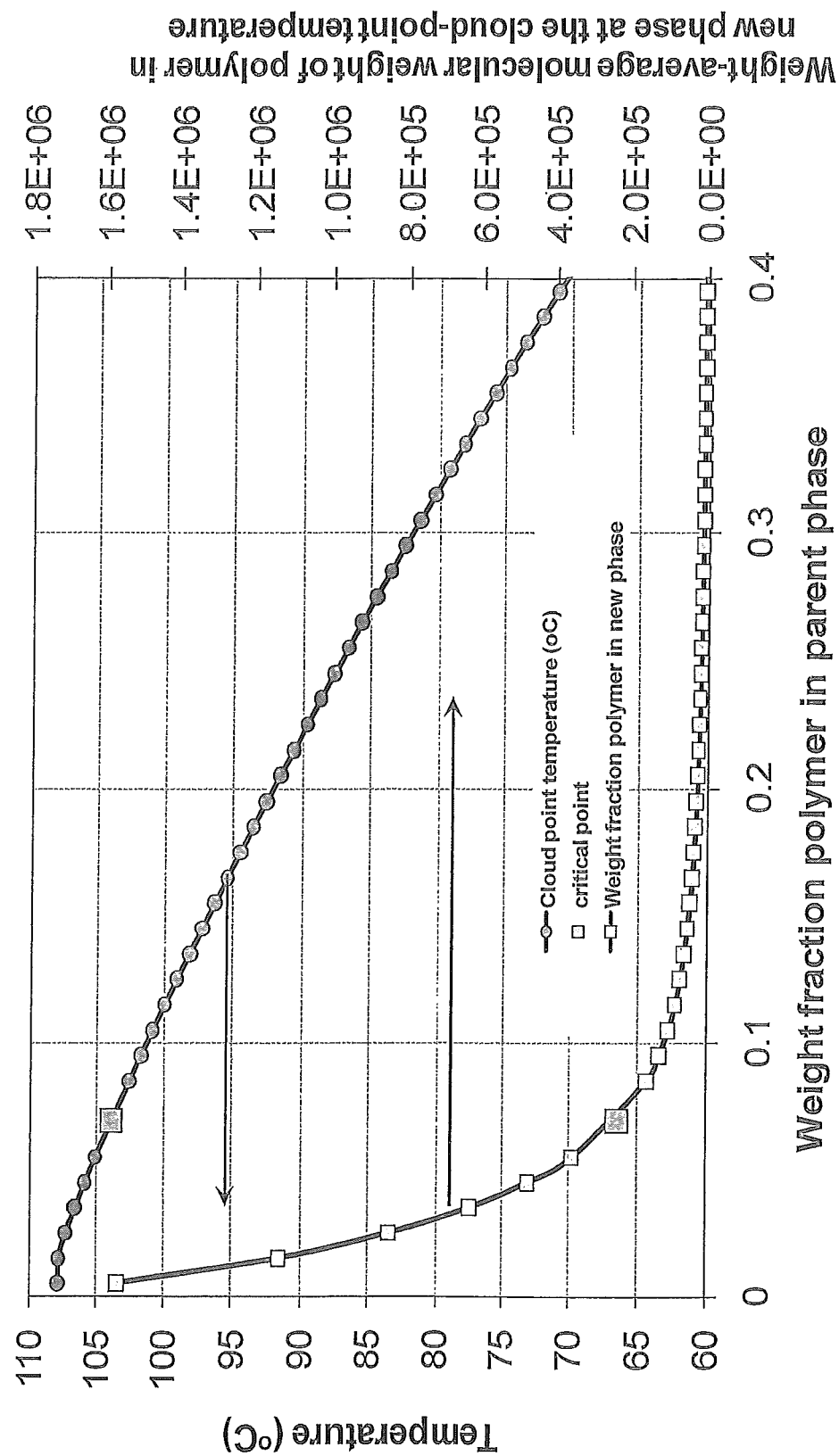
FIG. 4 is a calculated plot of the isobaric cloud point curve overlaid with a curve showing the magnitude of the weight-average molecular weight of polymer in the new phase formed at the cloud point. for commercial polyethylene LFY320C, based on the Sanchez-Lacombe equation of state.

Flash calculations were also performed to examine the composition of the phases formed below the liquid liquid phase boundary. FIG. 4 is a calculated plot of the isobaric cloud point curve overlaid with a curve showing the magnitude of the weight-average molecular weight of polymer in the new phase formed at the cloud point for commercial polyethylene LFY320C, based on the Sanchez-Lacombe equation of state. Initial solutions whose polymer concentration is less than the critical value yield new phases with polymer of higher molecular weight than the parent phase, and can have weight average molecular weights of about 500,000 and above. It also shows that solutions whose polymer concentration is larger than the critical yield new phases of low molecular weight.

The phase equilibrium calculations described above indicate that phase separation of polymer solutions whose concentration is below the critical value will yield a new liquid phase containing polymer of very high molecular weight. For pressures similar to those in the reactor, this phase separation will occur at temperatures near about 100° C., depending on the polymer concentration and molecular weight distribution. There are no measurements of the crystallization temperature of polyethylene in ethylene solutions. The likely reason for this is that cooling solutions of polyethylene will initially result in liquid-liquid phase separation and this can mask the detection of the solid-liquid boundary (since crystallization measurements at very high pressure are usually made by observing the cloudiness of the solution as crystals are formed, similar to the formation of the liquid-liquid system). As the system is cooled below the cloud point, the phase containing the higher molecular weight polymer/gel and higher polymer concentration will eventually precipitate to yield semi crystalline polymer.

Figure 5:
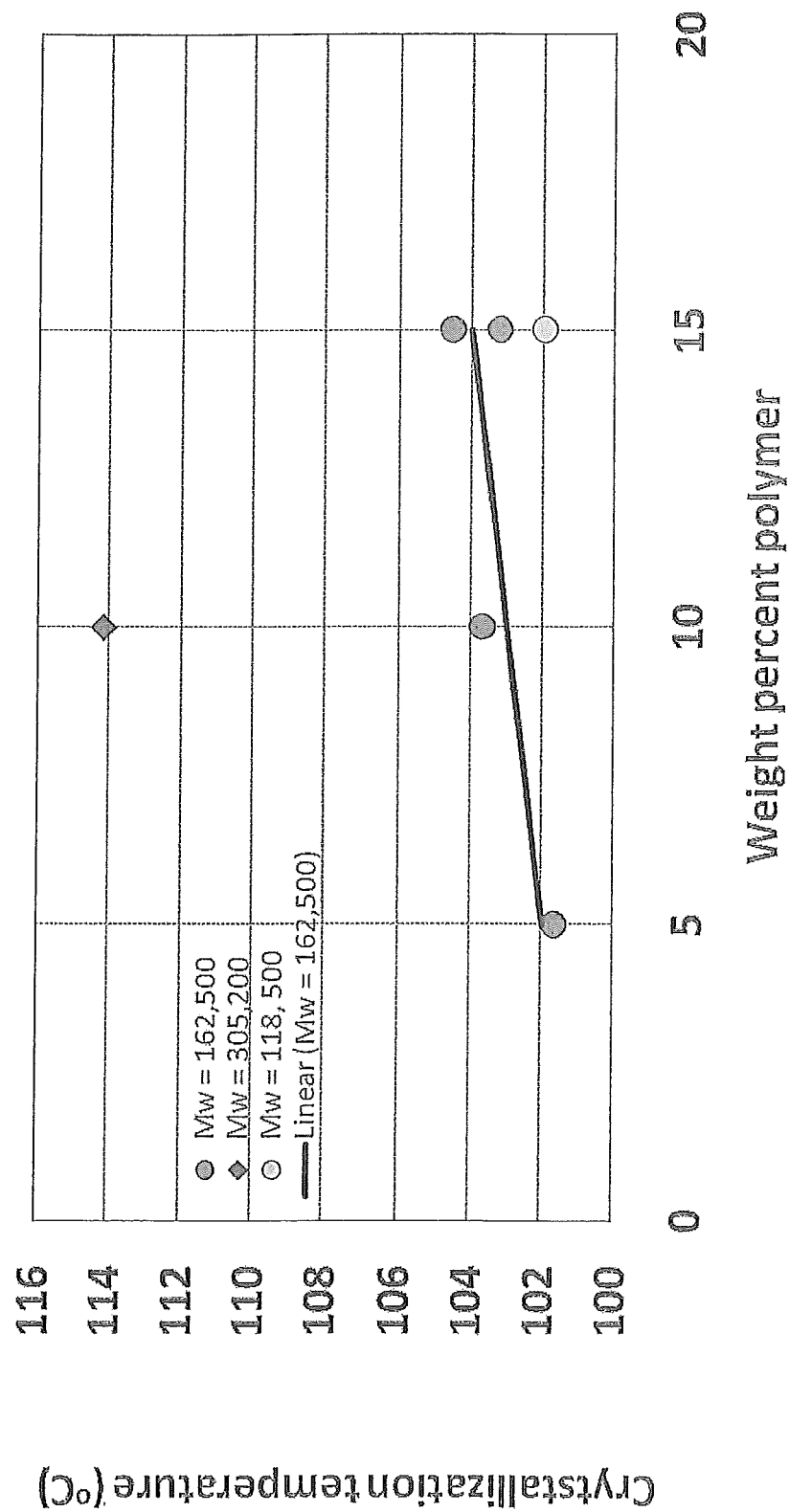
FIG. 5 shows the crystallization temperature of solutions of polyethylene in isohexane under shear.

Since there are no data for polymer crystallizing in ethylene solutions, it is useful to look at data for the crystallization of polymer in other hydrocarbon solvents. FIG. 5 shows the crystallization phase boundary of solutions of polyethylene in isohexane under shear. Solutions of these polydisperse polyethylene samples crystallize at temperatures above about 100° C., and the change in molecular weight from about 162,500 to about 305,200 increases the crystallization temperature by about −10° C. This suggests that in a tubular LDPE reactor, the disperse liquid phase containing extremely high molecular weight gel have a crystallization temperature of the order of about 110° C. or more. This is consistent with observations on reactor tubes that have been removed from service, which can have a high molecular weight polyethylene coating on the inner wall.

In the last few years, a more popular equation of state (EOS) for modeling high pressure polymer solutions has been the Statistical Associating Fluid Theory (SAFT) EOS (Chapman, W. G.; Gubbins, K. E.; Jackson, G.; Radosz, M. New Reference Equation of State for Associating liquids. Ind. Eng. Chem. Res. 1990, 29, 1709. Huang, S. H.; Radosz, M. Equation of State for Small, Large, Polydisperse, and Associating Molecules. Ind. Eng. Chem. Res. 1990, 29, 2284. Huang, S. H.; Radosz, M. Equation of State for Small, Large, Polydisperse and Associating Molecules: Extensions to Fluid Mixtures. Ind. Eng. Chem. Res. 1991, 30, 1994. Erich A. Müller; Keith E. Gubbins, Molecular-Based Equations of State for Associating Fluids: A Review of SAFT and Related Approaches, Ind. Eng. Chem. Res., 2001, 40, 2193.). The Perturbed-Chain SAFT EOS is an improved form of the original SAFT EOS.

Figure 6:
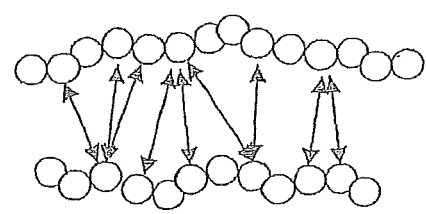
FIG. 6 is a schematic diagram of dispersion interactions of two n-alkane chains of covalently bonded spheres based on an averaged radial distribution function showing reaction between indistinguishable segments of the chains.
Figure 7:
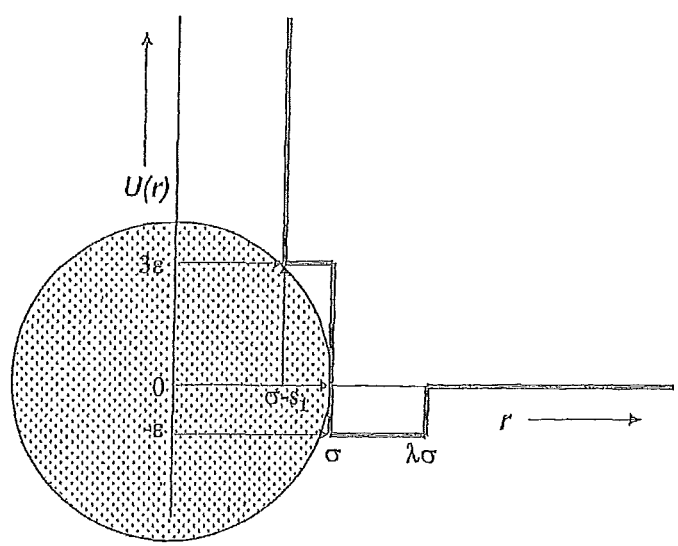
FIG. 7 is diagram of the inter-segment potential energy function used in the PC-SAFT equation of state.

The PC-SAFT EOS, molecules are conceived as chains composed of spherical segments, as shown in FIG. 6. In FIG. 6 the arrows are representative of the interaction between N-alkane ($CH_2$) segments. The interactions are based on the average radial distribution function between indistinguishable segments on one chain with those on another. The intermolecular potential energy function describing the interaction between segments, which distinguishes PC-SAFT from SAFT, is given by the modified square-well potential suggested by Chen and Kreglewski (Applications of the Augmented van der Waals Theory of Fluids. I. Pure Fluids. *Ber. Bunsen-Ges. Phys. Chem.*, 1977, 81, 1048-1052) and is illustrated in FIG. 7.

In this figure, the circle represents a spherical segment of a molecule chain, the bold line represents the intermolecular potential energy, u(r)(in J) is the inter-segment potential energy function, r(in Å) is the radial distance from the middle of a segment, $\sigma$ (in Å) is the temperature-independent segment diameter, $\epsilon$ (in J) the depth of the potential energy well, and $\lambda$ the reduced square-well width, with $s_1$ being fixed at $0.12\sigma$. The 'step' in the potential energy function (the step from $3\epsilon$ to $-\epsilon$) accounts for an essential feature of real molecule behavior, namely soft repulsion. Based on this picture, molecules of each pure compound are characterized by three pure compound parameters: the temperature-independent segment diameter, $\sigma$ (Å); the depth of the potential energy well $\epsilon$ (J); and the number of segments in each chain, m. The number of segments in the chain relates to the molecular weight.

In the original SAFT EOS, the Helmholtz energy of the reference fluid, $A^{hc}$, which is a chain of bonded hard spheres was obtained as a sum of terms accounting for the repulsive energy of non-interacting hard spheres, $A^{hs}$, the energy of forming chains from these spheres through covalent bonding, $A^{cf}$, and the energy of forming clusters (association) via, say, hydrogen bonding, $A^{ass}$, i.e.

$$A^{hc} = A^{hs} + A^{cf} + A^{ass} \tag{10}$$

The PC-SAFT EOS uses the same terms. However, the systems examined in this study do not exhibit association and this term is set to zero, so that for the PC-SAFT EOS:

$$A^{hc} = A^{hs} + A^{cf} \tag{11}$$

Returning to equation (10), in the PC-SAFT EOS, the Boublik (Boublik, T. Hard-Sphere Equation of State. J. Chem. Phys. 1970, 53, 471) and Mansoori et al (Mansoori, G. A.; Carnahan, N. F.; Starling, K. E.; Leland, T. W. Equilibrium Thermodynamic Properties of the Mixture of Hard Spheres. J. Chem. Phys. 1971, 54, 1523) expression for the Helmholtz energy of a mixture of monomeric non-attracting hard sphere segments is used:

$$\frac{A^{hs}}{n_t RT} = \overline{m} \tilde{a}^{hs} = \frac{\overline{m}}{\zeta_0} \cdot \left[ \frac{3\zeta_1 \zeta_2}{(1-\zeta_3)} + \frac{\zeta_2^3}{\zeta_3(1-\zeta_3)^2} + \left( \frac{\zeta_2^3}{\zeta_3^2} - \zeta_0 \right) \cdot \ln(1-\zeta_3) \right] \tag{12}$$

where $\tilde{a}^{hs}$ is the reduced molar Helmholtz energy of hard sphere monomers, per mole of segments [hence the factor $\overline{m}$ in equation (12)]. The average number of segments in the solution is $$\overline{m} = \sum_i x_i m_i,$$

with $$\zeta_n = \frac{\pi}{6} \rho \sum_{i=1}^{N_C} x_i m_i d_i^n \tag{13}$$

$$n \in \{0, 1, 2, 3\}$$

$m_i$ is the number of segments in a chain of component i and $d_i$ (Å) is the temperature dependent diameter of the monomeric hard sphere segments (Chen and Kreglewski, 1977):

$$d_i(T) = \sigma_i \cdot \left(1 - 0.12 \cdot \exp\left(-\frac{3 \cdot \varepsilon_i}{kT}\right)\right) \tag{14}$$

which is a function of the previously described temperature-independent parameters $\sigma_i$ (Å) and $(\varepsilon/k)_i$ (K) for component i. The packing fraction, $\zeta_3 = \eta$, is the ratio of the volume occupied by the segments to the total volume available.

The chain formation Helmholtz energy term in equation (10), used in the SAFT EOS, is described by Chapman et al (1990). This accounts for the change in Helmholtz energy due to creating covalent bonds from monomeric spherical segments and has the following form:

$$\frac{A^{cf}}{n_t Rt} = \tilde{a}^{cf} = \sum_{i=1}^{N_C} x_i (1 - m_i) \rho \ln [g_{ii}^{hs}(\sigma_{ii})] \tag{15}$$

where $\tilde{a}^{cf}$ is the reduced molar Helmholtz energy of chain formation, per mole of chains and $g_{ii}^{hs}(\sigma_{ii})$ is the hard sphere pair correlation (or radial distribution) function for the interaction of two spheres i and j in a mixture of spheres, evaluated at the hard sphere contact distance, $\sigma_{ij}$:

$$g_{ij}^{hs}(\sigma_{ij}) = \frac{1}{(1-\zeta_3)} + \left(\frac{d_i d_j}{d_i + d_j}\right) \frac{3\zeta_2}{(1-\zeta_3)^2} + \left(\frac{d_i d_j}{d_i + d_j}\right)^2 \frac{2\zeta_2^2}{(1-\zeta_3)^3} \tag{16}$$

Equations (11), (12) and (15) are used to calculate $A^{hc}$ in PC-SAFT EOS.

The total Helmholtz energy of the system, A, is given by:

$$A = A^{id} + A^{hc} + A^{pert} \tag{17}$$

where $A^{id}$, $A^{hc}$, and $A^{pert}$ are the ideal gas, hard sphere chain and perturbation contributions to the Helmholtz energy. The ideal gas contribution to the Helmholtz energy $A^{id}$ has the following form, for a system of Nc components with mole fractions $x_i$:

$$\frac{A^{id}}{n_t RT} = \tilde{a}^{id} = \sum_{i=1}^{N_C} x_i \ln(\rho_i \Lambda_i^3) - 1 \tag{18}$$

where $\tilde{a}^{id}$ is the reduced ideal gas Helmholtz energy per mole of chains, $$\rho_i = \frac{N_i}{V},$$

the number density of component i where $N_i$ is the number of chains of component i and V is the total volume available. The temperature is T, $n_t$ the total number of moles, $\Lambda_i$ the de Broglie wavelength of component i and R is the Ideal Gas constant. The de Broglie wavelength of component i with chains of mass $m_{pi}$ is given by:

$$\Lambda_i = \sqrt{\frac{2\pi m_{pi} kT}{h^2}} \tag{19}$$

Where h is Planck's constant and k is Boltzmann's constant. This expression yields a compressibility factor equal to 1 upon differentiation, as expected for an ideal gas.

The last term in the Helmholtz energy, equation (17), $A^{pert}$, arises from attractive 'dispersion' interactions and distinguishes the PC-SAFT EOS from the original SAFT EOS. In most thermodynamic perturbation theories (Boublik, T.; Perturbation Theory, Chapter 2 in Equations of State for Fluids and Fluid Mixtures Part 1, Sengers, J. V.; Kayser, R. F.; Peters, C. J.; White, H. J.; (eds.), 2000, Elsevier Science, NY.), it is equated directly to the dispersion energy, i.e., $A^{pert} = A^{disp}$. In the original SAFT EOS, the perturbation contribution is based on the dispersion energy due to interactions between isolated spheres, adjusted to reflect the real behaviour of argon (Chen and Kreglewski, 1977), but PC-SAFT is based on multi-sphere bonded chains, in the form of the homologous series of n-alkanes (n-$C_1$ to n-$C_{30}$). In the PC-SAFT EOS, this perturbation contribution is obtained from Barker and Henderson's (Barker, J. A.; Henderson, D.; Perturbation Theory and Equation of State for Fluids. II. A Successful Theory for liquids. J. Chem. Phys., 1967, 47, 4714-4721) 2nd order perturbation theory as a sum of first ($A_1$) and second ($A_2$) order perturbation terms:

$$\frac{A^{pert}}{n_t RT} = \frac{A^{disp}}{n_t RT} = \tilde{a}^{disp} \cong \frac{A_1}{n_t RT} + \frac{A_2}{n_t RT} \qquad (20)$$

where $\tilde{a}^{disp}$ is the residual Helmholtz energy due to dispersion forces, per mole of chains. Gross and Sadowski (2001) applied Barker and Henderson's theory to a system of chain molecules interacting via a square-well potential using Chiew's (1991) expression for the radial distribution function of interacting hard chains. They approximated the resulting two integrals of the radial distribution function in $A_1$ and $A_2$ using a temperature-independent power series ranging to 6th order in packing fraction ($\eta$) and dependent on the average number of segments in the molecule ($\bar{m}$). For a mixture, the integral in $A_1$ is given by the expression $$I_1(\eta, \bar{m}) = \int_1^\infty \tilde{u}(x) g^{hc}\left(\bar{m}; x \cdot \frac{\sigma}{d}\right) x^2 \, dx = \sum_{i=1}^{6} a_i(\bar{m}) \eta^i \qquad (21)$$

with the function $a_i(\bar{m})$ given by $$a_i(\bar{m}) = a_{0i} + \frac{\bar{m}-1}{\bar{m}} a_{1i} + \frac{\bar{m}-1}{\bar{m}} \frac{\bar{m}-2}{\bar{m}} a_{2i} \qquad (22)$$

where $\{a_{0i}, a_{1i}, a_{2i}, 1 \leq i \leq 6\}$ are adjustable constants. The integral in $A_2$ is represented by a similar function:

$$I_2(\eta, \bar{m}) = \frac{\partial}{\partial \rho} \left\{ \rho \int_1^\infty (\tilde{u}(x))^2 g^{hc}\left(\bar{m}; x \cdot \frac{\sigma}{d}\right) x^2 \, dx \right\} = \sum_{i=1}^{6} b_i(\bar{m}) \eta^i \qquad (23)$$

with the function $b_i(\bar{m})$ being given by:

$$b_i(\bar{m}) = b_{0i} + \frac{\bar{m}-1}{\bar{m}} b_{1i} + \frac{\bar{m}-1}{\bar{m}} \frac{\bar{m}-2}{\bar{m}} b_{2i} \qquad (24)$$

where $\{b_{0i}, b_{1i}, b_{2i}, 1 \leq i \leq 6\}$ are adjustable constants. The constants in equations (22) and (24) were determined by fitting pure component data for n-alkanes. First the integrals were fully evaluated for Lennard-Jones (LJ) chains, using the expressions in the note above and an averaged radial distribution function for segments in LJ chains, and n-alkane vapour pressure and density data were regressed to obtain the values of three pure compound parameters m, $\sigma$ and $\epsilon/k$ (the segment number, segment diameter and reduced interaction energy magnitude, where k (J/K) is Boltzmann's constant). Once this was done, the constants in the polynomial expressions for the integrals were evaluated for n-alkanes, from methane to triacontane, using vapour pressure, liquid, vapour and supercritical density data. Hence, the PC-SAFT equation reproduces n-alkane data accurately. Optimal values of the adjustable constants $\{a_{0i}, a_{1i}, a_{2i}, b_{0i}, b_{1i}, b_{2i}, 1 \leq i \leq 6\}$ are listed below

| Values of Universal Constants in the PC-SAFT EOS | | | | | | |
|---|---|---|---|---|---|---|
| I | $a_{0i}$ | $a_{1i}$ | $a_{2i}$ | $b_{0i}$ | $b_{1i}$ | $b_{2i}$ |
| 0 | 0.9105631445 | −0.3084016918 | −0.0906148351 | 0.7240946941 | −0.5755498075 | 0.0976883116 |
| 1 | 0.6361281449 | 0.1860531159 | 0.4527842806 | 2.2382791861 | 0.6995095521 | −0.2557574982 |
| 2 | 2.6861347891 | −2.5030047259 | 0.5962700728 | −4.0025849485 | 3.8925673390 | −9.1558561530 |
| 3 | −26.547362491 | 21.419793629 | −1.7241829131 | −21.003576815 | −17.215471648 | 20.642075974 |
| 4 | 97.759208784 | −65.255885330 | −4.1302112531 | 26.855641363 | 192.67226447 | −38.804430052 |
| 5 | −159.59154087 | 83.318680481 | 13.776631870 | 206.55133841 | −161.82646165 | 93.626774077 |
| 6 | 91.297774084 | −33.746922930 | −8.6728470368 | −355.60235612 | −165.20769346 | −29.666905585 |

For application to other fluids, the constants in the expressions for the integrals are set to the values optimized for n-alkanes, and hence are assumed to be universal for all compounds. The values of the three pure compound parameters; the segment number, m, the segment diameter, $\sigma$, and the reduced interaction energy, $\epsilon/k$ are then fit to pure compound data for the compound of interest. The EOS was extended to mixtures using the usual one fluid mixing rules incorporating a binary interaction parameter $k_{ij}$ to correct the segment-segment interaction energies of unlike chains. Hence the final form of the Helmholtz energy is:

$$\tilde{a}^{disp} = \frac{A_1}{n_t RT} + \frac{A_2}{n_t RT} \qquad (25)$$

with $$\frac{A_1}{n_t RT} = -2\pi \rho I_1(\eta, \bar{m}) \overline{m^2 \epsilon \sigma^3} \qquad (26)$$

and a one-fluid quadratic mixing rule for the segment diameter and energy-well parameter $$\overline{m^2 \epsilon \sigma^3} = \sum_{i=1}^{N_C} \sum_{j=1}^{N_C} x_i x_j m_i m_j \left(\frac{\epsilon_{ij}}{kT}\right) \sigma_{ij}^3 \qquad (27)$$

The mixture segment diameter between pairs of segments is calculated as an arithmetic average $$\sigma_{ij} = \frac{1}{2}(\sigma_i + \sigma_j) \qquad (28)$$

while the mixture potential well-depth of FIG. 2 is obtained from geometric averaging, with a binary interaction parameter to correct for asymmetry:

$$\epsilon_{ij} = \sqrt{\epsilon_i \epsilon_j} \cdot (1 - k_{ij}) \qquad (29)$$

As usual, the value of the binary interaction parameter $k_{ij}$ is obtained by fitting phase equilibrium data.

The same experimental data was used to fit the system-dependent parameters to the PC-SAFT equation of state, those of Chun Chan et al. (2000) and Trumpi et al. (2003).

When the solving equations of state using the data developed using the above methods the calculations fit the actual measured data at each of the data points but was less than desirable between the data points. Hence, a decision was made to regress new values of the liquid liquid parameters $\epsilon_{ii}$ and binary interaction parameters $k_{ij}^a$ and $k_{ij}^b$. The EOS parameters were fit to the data to provide a good compromise between the two sets of data.

It was found that using the regressed values in the liquid liquid equation of state and breaking a polymer's molecular weight distribution into a set of pseudocomponents at least about 80, or about 100, or about 120 or greater) provided a good fit with the physical properties of the polymer.

Figure 8:
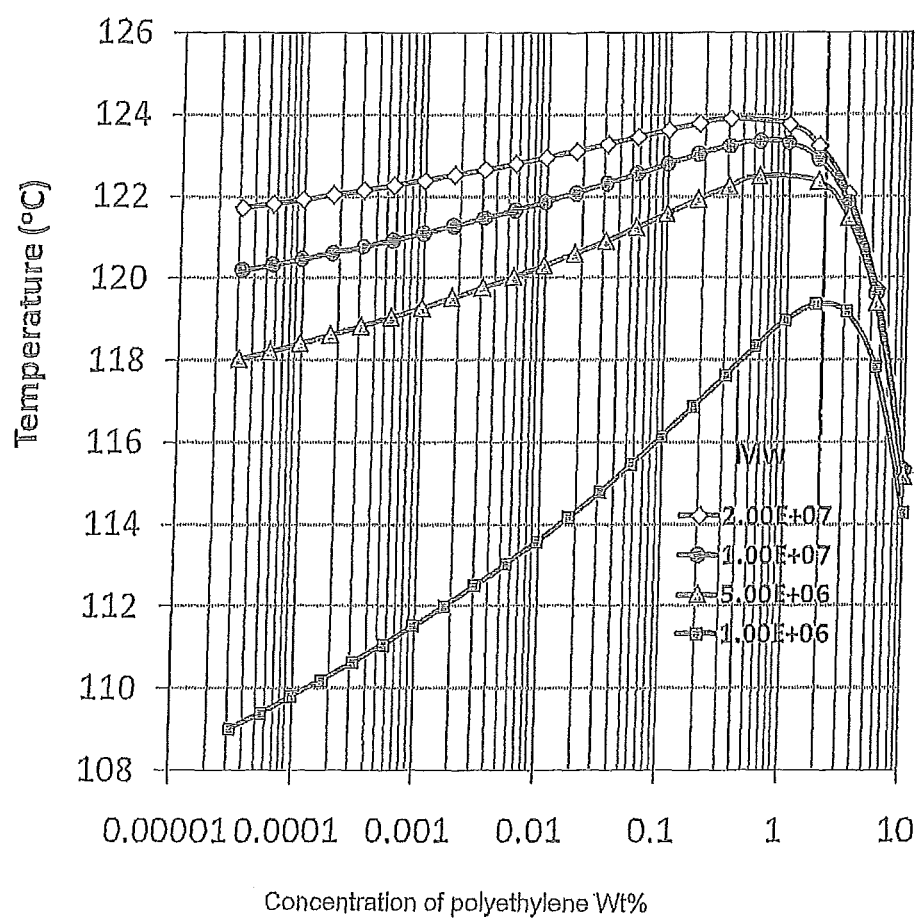
FIG. 8 is a calculated plot of cloud point (temperature of phase separation) as a function of polymer concentration for various molecular weights of polyethylene in an ethylene solution at a pressure of 200 MPa.

FIG. 8 illustrates the liquid-liquid phase boundary calculated for monodisperse polyethylene in supercritical ethylene at about 210 MPa, using the PC-SAFT equation of state. The results obtained with this model are similar to those obtained with the Sanchez-Lacombe equation of state.

One further advantage of an embodiment of the present invention is that it provides a method to closely approximate the equations of state for a polyethylene polymer for which there is a molecular weight distribution curve (e.g. SEC graph).

The present invention has been described with reference to certain details of particular embodiments thereof. It is not intended that such details be regarded as limitations upon the scope of the invention except insofar as and to the extent that they are included in the accompanying claims.

What is claimed is:

1. A method to determine the curve of the liquid liquid equilibrium boundary as a function of molecular weight distribution (MWD) for a multitude of different products comprising from about 80 to about 100 wt. % of ethylene and about 0 up to about 20 weight % of one or more $C_{3-8}$ alpha olefins having a molecular weight from about 8,000 to about 500,000 produced in super critical ethylene in a high pressure reactor at temperatures from about 80° C. to about 350° C. and pressures from about 100 MPa to about 350 MPa comprising:
   a) modeling experimental or literature data for the liquid liquid equilibrium using an equation of state model to describe the effects of the molecular weight and the polydispersity of the polyethylene on the liquid liquid equilibrium curve
   b) determining the composition-specific parameters of the model from a); and,
   c) applying the resultant Sanchez-Lacombe equation of state model to the temperature, pressure and composition conditions of the reaction to generate the liquid liquid equilibrium boundary and optionally the critical polymer concentration.

2. The process according to claim 1 wherein the reactor is a tubular reactor.

3. A process to prepare a liquid polymer lean/liquid polymer rich and liquid liquid phase diagram for a reactor for polymerizing a system comprising a polymer having a weight average molecular weight from about 8,000 to about 500,000 comprising from about 80 to about 100 wt % of ethylene and about 0 to about 20 wt % of one or more $C_{3-8}$ alpha olefins in super critical liquid ethylene at temperatures from about 80° C. to about 350° C. and pressures from about 100 MPa to about 350 MPa to define operating conditions at which the polymer is substantially dissolved in the liquid phase comprising:
   preparing a phase diagram for liquid polymer lean/liquid polymer rich for said reactor and process at temperatures from about 150° C. to about 350° C. and pressures from about 100 to about 350 MPa;
   A) inserting into said phase diagram a liquid liquid phase boundary determined according to claim 1.

4. A method for conducting the polymerization of a polymer having a weight average molecular weight from about 8,000 to about 500,000 comprising about 80 to about 100 wt % of ethylene and about 0 to about 20 wt. % of one or more $C_{3-8}$ alpha olefins in super critical liquid ethylene at temperatures from about 80° C. to about 350° C. and pressures from about 100 MPa to about 350 MPa to define operating conditions at which the polymer is substantially dissolved in the liquid phase comprising monitoring the heat balance of said reaction and determining when there is an apparent loss of cooling and comparing the operating conditions to the phase diagram according to claim 3, and adjusting one or more of the temperature and pressure conditions to bring the operating conditions more than about 5% more within the liquid area of the phase diagram.

5. The method according to claim 4, wherein the operating conditions are adjusted to bring them within the liquid area of the phase diagram by more than about 10%.

6. The method according to claim 5, wherein the phase diagram is digitized and stored on a microprocessor and heat balance for the reaction is monitored using a microprocessor and the operating conditions are adjusted using a microprocessor.

7. A method to extend the run time between cleanings of a high pressures reactor for the polymerization of a polymer having a weight average molecular weight from about 8,000 to about 500,000 comprising about 80 to about 100 wt % of ethylene and about 0 to about 20 wt % of one or more $C_{3-8}$ alpha olefins in super critical ethylene at temperatures from about 80° C. to about 350° C. and pressures from about 100 MPa to about 350 MPa comprising operating according to claim 5, so that not more than about 30 minutes elapse between the apparent loss of cooling and achieving the new operating conditions within the liquid area within the phase diagram.

8. The method according to claim 7, wherein the time to achieve the adjusted operating conditions is less than about 15 minutes.

9. A method to dissolve precipitated polymer in a high pressures reactor for the polymerization of a polymer having a weight average molecular weight from about 8,000 to about 500,000 comprising about 80 to about 100 wt % of ethylene and about 0 to about 20 wt % of one or more $C_{3-8}$ alpha olefins in super critical liquid ethylene at temperatures from about 80° C. to about 350° C. and pressures from about 100 MPa to about 350 MPa comprising operating according to claim 7, so that not more than about 30 minutes elapse between the apparent loss of cooling and achieving the new operating conditions within the liquid area within the phase diagram.

10. The method according to claim 9, wherein the phase diagram is digitized and stored on a microprocessor and heat balance for the reaction is monitored using a microprocessor and the operating conditions are adjusted using a microprocessor.

11. The method according to claim 10 wherein the time to achieve the adjusted operating conditions is less than about 15 minutes.

* * * * *